US009750593B2

(12) United States Patent
Meneghin et al.

(10) Patent No.: US 9,750,593 B2
(45) Date of Patent: Sep. 5, 2017

(54) MARKED PROSTHESIS

(75) Inventors: Alfredo Meneghin, Laval (FR); Xavier Bourges, Saint Etienne sur Chalaronne (FR); Julie Lecuivre, Le Bois d'Oingt (FR)

(73) Assignee: SOFRADIM PRODUCTION, Trevoux (FR)

( * ) Notice: Subject to any disclaimer, the term of this patent is extended or adjusted under 35 U.S.C. 154(b) by 619 days.

(21) Appl. No.: 13/810,499

(22) PCT Filed: Jul. 15, 2011

(86) PCT No.: PCT/EP2011/062147
§ 371 (c)(1),
(2), (4) Date: Mar. 8, 2013

(87) PCT Pub. No.: WO2012/007578
PCT Pub. Date: Jan. 19, 2012

(65) Prior Publication Data
US 2013/0158571 A1    Jun. 20, 2013

(30) Foreign Application Priority Data
Jul. 16, 2010 (FR) ..................... 10 55796

(51) Int. Cl.
*A61F 2/02* (2006.01)
*A61F 2/00* (2006.01)
(Continued)

(52) U.S. Cl.
CPC ............ *A61F 2/0063* (2013.01); *D04B 21/12* (2013.01); *A61F 2/0045* (2013.01);
(Continued)

(58) Field of Classification Search
CPC .... A61F 2002/30714; A61F 2210/0004; A61F 2220/0083; A61F 2250/0062;
(Continued)

(56) References Cited

U.S. PATENT DOCUMENTS 4,259,959 A * 4/1981 Walker .................. A61B 17/08
606/213
4,548,202 A * 10/1985 Duncan .............. A61B 17/0643
606/220
(Continued)

FOREIGN PATENT DOCUMENTS

CN    101489502 A    7/2009
DE    19636961 A1    3/1998
(Continued)

OTHER PUBLICATIONS

International Search Report corresponding to International Application No. PCT/EP2011/062147, date of completion was Aug. 16, 2011 and date of mailing was Aug. 24, 2011; (2 Pages).
(Continued)

*Primary Examiner* — Julian W Woo

(57) ABSTRACT

The present invention relates to a prosthesis (10) intended to be implanted at an implantation site, comprising information means designed to guide the surgeon in order to implant the prosthesis in a specified position, said prosthesis comprising at least one fabric called the base fabric (2) and having at least one apertured surface (3), said information means comprising at least one patch (4, 5) having a color different from that of the base fabric, said patch being provided with at least one barb (6) projecting from one of its surfaces and grippingly fastening said patch to said apertured surface of said base fabric at a specific place on said surface, the presence of said patch at said specific place bearing information designed to facilitate implantation of the prosthesis in said specified position. The invention also relates to a kit comprising a fabric and a patch.

21 Claims, 1 Drawing Sheet

(51) Int. Cl.
*D04B 21/12* (2006.01)
*A61F 2/30* (2006.01)

(52) U.S. Cl.
CPC .............. *A61F 2002/30714* (2013.01); *A61F 2210/0004* (2013.01); *A61F 2220/0083* (2013.01); *A61F 2250/005* (2013.01); *A61F 2250/0062* (2013.01); *A61F 2250/0087* (2013.01); *A61F 2250/0089* (2013.01); *A61F 2250/0097* (2013.01); *D10B 2403/0213* (2013.01); *D10B 2501/0632* (2013.01); *D10B 2509/08* (2013.01)

(58) Field of Classification Search
CPC ...... A61F 2250/0087; A61F 2250/0089; A61F 2250/0097; A61F 2/0045; A61F 2/0063; A61F 2250/005; D04B 21/12; D10B 2403/0213; D10B 2501/0632; D10B 2509/08
See application file for complete search history.

(56) References Cited

U.S. PATENT DOCUMENTS

| | | | | |
|---|---|---|---|---|
| 4,633,873 | A * | 1/1987 | Dumican et al. | 606/151 |
| 6,241,768 | B1 | 6/2001 | Agarwal et al. | |
| 6,645,226 | B1 * | 11/2003 | Jacobs et al. | 606/215 |
| 7,011,688 | B2 * | 3/2006 | Gryska | A61F 2/0063 600/37 |
| 7,021,316 | B2 * | 4/2006 | Leiboff | A61B 17/0401 128/898 |
| 7,641,958 | B2 * | 1/2010 | Berman | A61L 17/04 428/141 |
| 7,828,854 | B2 * | 11/2010 | Rousseau et al. | 623/23.72 |
| 8,562,633 | B2 * | 10/2013 | Cully | A61F 2/0063 606/151 |
| 8,579,922 | B2 * | 11/2013 | Glick et al. | 606/148 |
| 8,968,418 | B2 * | 3/2015 | Paul | A61F 2/0063 623/23.72 |
| 2002/0077661 | A1 | 6/2002 | Saadat | |
| 2004/0019360 | A1 * | 1/2004 | Farnsworth | A61F 2/0063 606/151 |
| 2004/0054376 | A1 * | 3/2004 | Ory | A61F 2/0063 606/151 |
| 2008/0167729 | A1 | 7/2008 | Nelson et al. | |
| 2009/0036907 | A1 * | 2/2009 | Bayon et al. | 606/151 |
| 2011/0082478 | A1 | 4/2011 | Glick et al. | |
| 2011/0125188 | A1 * | 5/2011 | Goraltchouk | A61B 17/06166 606/228 |
| 2013/0060263 | A1 * | 3/2013 | Bailly | A61F 2/0063 606/151 |

FOREIGN PATENT DOCUMENTS

| | | |
|---|---|---|
| FR | 2 875 396 A1 | 3/2006 |
| FR | 2 914 179 A1 | 10/2008 |
| JP | H11146888 A | 6/1999 |
| JP | 2008538300 A | 10/2008 |
| JP | 2011078767 A | 4/2011 |
| JP | 2012516747 A | 7/2012 |
| WO | 2006032812 A2 | 3/2006 |
| WO | 2006102374 A2 | 9/2006 |

OTHER PUBLICATIONS

Chinese Office Action, Application No. 2011800426371 issued May 20, 2015.

Japanese Office Action mailed Sep. 17, 2015 in corresponding Japanese Patent Application No. 2013-519112.

Japanese Notice of Allowance issued Apr. 13, 2016 in corresponding Japanese Patent Application No. 2013-519112, 3 pages.

* cited by examiner

MARKED PROSTHESIS

CROSS-REFERENCE TO RELATED APPLICATIONS

This application is a U.S. National Stage Application filed under 35 U.S.C. §371(a) of International Application No. PCT/EP2011/062147 filed Jul. 15, 2011, which claims the benefit of and priority to French Patent Application Serial No. 10/55796 filed Jul. 16, 2010, the entire contents of which are incorporated by reference herein.

The present invention relates to a prosthesis based on a fabric and comprising information means for the surgeon, designed to facilitate the implantation of the prosthesis in a specified position.

Many prostheses, such as for example abdominal wall reinforcements or urinary incontinence pads, take the form of a piece of biocompatible fabric, which may or may not be accompanied by additional elements such as, for example, a coating in the form of a film, reinforcing elements, a set of needles, etc. The piece of fabric of these prostheses are often of symmetrical shape. This is in particular the case of prostheses for reinforcing walls, for example abdominal walls, these being widely used in the surgical field and designed for treating hernias, by filling, either temporarily or definitely, a tissue failure. These prostheses may be of various shapes: rectangular, round, oval, etc., depending on the anatomical structure to which they have to adapt. Some of these prostheses are made from entirely biodegradable yarns and are intended to disappear after having carried out their reinforcing role until cell colonization takes place and tissue rehabitation takes over. Other prostheses comprise non-biodegradable yarns and are intended to remain permanently in the patient's body.

In any case, for safety reasons, these prostheses must often be positioned in a specific and very precise way with respect to the surrounding organs at the moment of implantation. Thus, it is sometimes necessary to provide these prostheses with markers or information means for the purpose of providing the surgeon with indications about the particular properties of one surface of the fabric or else about the dimensions or the location of a precise point on the piece of fabric.

Thus, depending on the environment of the implantation site, for example in the presence of viscera, soft tissue, etc., it may be important to give the surgeon indications at a given place on the fabric, so that he can position the piece of fabric in a particular orientation or else position a certain region of the prosthesis so as to face said organ or on the contrary to be as far as possible away from said organ, etc.

Prostheses based on a fabric comprising markers or information means already exist.

One solution for providing prostheses with markers is to give them coloured parts. For example, it is possible to deposit coloured ink directly on the yarns constituting the piece of fabric. However, such a solution has the drawback that the inks are not favourable for cell colonization. Thus, cell recolonization after implantation runs the risk of not taking place optimally at the point where the yarns of the prosthesis are covered with ink. In the case of hernia treatment, this means that part of the prosthesis will not be recolonized by the surrounding cells. The abdominal wall reinforcing role of the prosthesis will therefore not be optimal.

Moreover, there is no optimum visibility of the parts coloured with yarns on which ink has been deposited on apertured fabrics either, and it may happen that the surgeon is unable to see these coloured parts at the moment of implantation, thus loosing potentially precious information about the position of the prosthesis within the implantation site.

Another solution of the prior art consists in embroidering with suture thread: however, such a solution is tricky and time-consuming, namely the time needed to produce the embroidery. Moreover, the addition of embroidery on a fabric causes distortions of this fabric and excess neofibrosis may occur, depending on the density of the embroidery produced.

Thus, there remains a need to be able to provide the fabric of a prosthesis with information means reliably and rapidly without jeopardizing the effectiveness both of said information means and the prosthesis itself.

The aim of the present invention is to meet this need by providing a prosthesis based on a fabric, this being provided with information means easy to install on said fabric, and having no negative effect on the positioning of the prosthesis and on its effectiveness.

A first aspect of the present invention is a prosthesis intended to be implanted at an implantation site, comprising information means designed to guide the surgeon in order to implant the prosthesis in a specified position, said prosthesis comprising at least one fabric called the base fabric and having at least one apertured surface, said information means comprising at least one patch having a colour different from that of the base fabric, said patch being provided with at least one barb projecting from one of its surfaces and grippingly fastening said patch to said apertured surface of said base fabric at a specific place on said surface, the presence of said patch at said specific place bearing information designed to facilitate implantation of the prosthesis in said specified position.

The term "fabric" is understood in the context of the present application to mean any fabric obtained by an arrangement or assembly of biocompatible yarns, fibres, monofilaments and/or multifilaments, such as a knitted, woven, braided or non-woven fabric, and having two opposed surfaces.

At least one of the surfaces of the base fabric of the prosthesis according to the invention is apertured. The term "apertured surface" is understood according to the present application to mean that said surface of the fabric comprises openings, cavities, pores or holes that are open to the outside. Such openings promote the penetration of cells into the fabric and therefore cell recolonization of the prosthesis after implantation. As will become apparent in the rest of the description, the openings in the apertured surface of the base fabric of the prosthesis according to the invention have a size making them capable of receiving and retaining, by their walls formed by the yarns constituting the fabric, the barb or barbs of the patch or patches of the prosthesis according to the invention.

The prosthesis according to the invention may be produced in a particularly simple and rapid manner. Specifically, the base fabric of the prosthesis does not have to undergo any particular treatment to colour certain of its parts, with the risk of infection, distortion or damage that this entails. It is sufficient to provide the fabric with one or more patches that can be manufactured at the start from a biocompatible coloured material, for example a coloured material approved by the regulations in force in respect of medical devices, which are grippingly fastened to the base fabric at a particular place and provide particular information to the surgeon. The patches may be relatively small in size compared with the size of the prosthesis and of the base fabric, the difference in colour between the base fabric and the patch or patches generally being sufficient to draw the surgeon's attention thereto.

Thus, the prosthesis according to the invention, although provided with information means, loses none of the initial properties of the base fabric. In particular, the apertured surface of the base fabric of the prosthesis according to the invention maintains its good cell recolonization capability despite the presence of patches bearing information.

The information means of the prosthesis according to the invention may comprise a plurality of patches as described above, these being grippingly fastened at specific places on the apertured surface of the base fabric.

Thus, a patch may indicate a precise point on the base fabric, depending on the shape of the latter, such as its centre, or on the contrary at a point located at a certain distance from the centre or from the edge, or the cardinal points of the fabric, etc. Alternatively or in combination, a patch may simply indicate the apertured surface, as opposed to the opposite surface of the fabric, which may for example be closed off by an anti post-surgical adhesions film. A patch may also indicate that side via which the prosthesis must be inserted. For example, if the prosthesis has to be folded up on itself in order to be inserted into the implantation site, a patch may indicate the place or the line where the prosthesis has to be folded, etc.

The base fabric of the prosthesis according to the invention may have its two surfaces apertured. In such a case, one or more patches may be grippingly fastened to each of the two surfaces of the fabric, each patch being able to indicate one particular item of information from among the items of information described above.

The base fabric of the prosthesis according to the invention may be any fabric based on biocompatible yarns, filaments or fibres, such as a woven, a non-woven, a braid, a knit or a combination of the latter, provided that at least one of its surfaces is apertured.

The yarns, fibres or filaments and/or multifilaments forming the base fabric according to the invention may be made of any biocompatible material, whether biodegradable or not.

The term "biodegradable" or "bioresorbable" is understood in the context of the present application to mean the characteristic whereby a material is absorbed and degraded by biological tissues and disappears in vivo after a specified period of time which may vary, for example, from a few hours to several months, depending on the chemical nature of the material.

Thus, the biodegradable materials suitable for the yarns of the base fabric of the present invention may be chosen from polylactic acid (PLA), polyglycolic acid (PGA), oxidized cellulose, chitosan, polyphosphazene, polycaprolactone (PCL), polydioxanone (PDO), trimethylene carbonate (TMC), polyvinyl alcohol (PVA), polyhydroxyalkanoates (PHAs), polyamides, polyethers, copolymers thereof and blends thereof. Non-biodegradable materials suitable for the yarns of the base fabric of the present invention may be chosen from polyethylene terephthalate (PET), polyamides, aramids, expanded polytetrafluoroethylene, polyurethane, polyvinylidene fluoride (PVDF), butyl ester polymers, PEEK (polyetheretherketone), polyolefins (such as polyethylene or polypropylene), copper alloys, silver or platinum alloys, medical grades of steel such as medical-grade stainless steel, and combinations thereof.

In one embodiment of the invention, the base fabric is a knit: a knit, because of the meshes that make up the knit, provides apertured surfaces that are particularly well suited for the prosthesis according to the invention. The knit may be two-dimensional or three-dimensional.

The term "two-dimensional knit" is understood in the context of the present application to mean a knit having two opposed surfaces linked together by meshes but devoid of a spacer giving them a certain thickness: such a knit may for example be obtained by knitting yarns on a warp or Raschel knitting machine using two needle-guide bars. Examples of knitting two-dimensional knits suitable for the present invention, with at least one apertured surface, are given in document WO 2009/071998.

The term "three-dimensional knit" is understood according to the present application to mean a knit having two opposed surfaces linked together by a spacer giving the knit a significant thickness, said spacer itself being formed from additional linking yarns in addition to the yarns forming the two surfaces of the knit. Such a knit may for example be obtained on a double bed warp or Raschel knitting machine using several needle-guide bars. Examples of knitting three-dimensional knits suitable for the present invention, with at least one apertured surface, are given in the documents WO 99/05990, WO 2009/031035 and WO 2009/071998.

The base fabric of the invention may be a porous fabric or knit, i.e. one having cavities, pores or holes, not only on its surfaces but also within its thickness, these cavities, pores or holes being able to constitute channels emerging on either side of the fabric. Such a porous fabric allows better tissue integration, it being possible for cells to gain access to the interior of the fabric forming for example an abdominal wall reinforcement.

For example, the pattern of the base fabric may determine, within the thickness of the latter, a multiplicity of transverse cavities or channels, approximately parallel to one another, emerging on either side of said fabric on its two respective apertured surfaces, giving the fabric a "honeycomb" structure for example.

The patch or patches of the prosthesis according to the invention may be made of any biocompatible material, whether biodegradable or not, having a separate colour from that of the base fabric, the dye used to colour the material being recognized as biocompatible by the regulations in force regarding medical devices. For example, the patches may be made of a material chosen from nylon, polypropylene, polyethylene terephthalate (PET), polylactic acid (PLA), glycolic acid/lactic acid copolymer (GLA), polydioxanone and blends thereof. For example, if the base fabric is white in colour, patches coloured blue, violet or green, obtained using biocompatible dyes, may be chosen. For example: a nylon coloured blue with the dye FD&C Blue No. 2 (21 CFR 74.1102) may be obtained; a nylon coloured green with the dye D&C Green No. 5 (21 CFR 74.1109) may be obtained; a polypropylene coloured blue with the dye D&C Blue No. 6 (21 CFR 74.3106) may be obtained; a polyethylene terephtalate coloured blue with the dye D&C Blue No. 6 (21 CFR 74.3106) or green with the dye D&C Green No. 6 (21 CFR 74.3206) may be obtained; a glycolic acid/lactic acid copolymer (GLA) coloured green with the dye D&C Green No. 6 (21 CFR 74.3206) may be obtained and a polydioxanone coloured violet with the dye D&C Violet No. 2 (21 CFR 74.3602) may be obtained.

Thus, the patch or patches are directly visible to the surgeon who has to implant the prosthesis, and the information carried by the patch or patches is directly accessible to him. In one embodiment of the invention, the patch is made of polyethylene terephtalate.

In one embodiment of the invention, the patches are made of biodegradable material, as defined above. Examples of biodegradable materials suitable for the manufacture of the patches of the prosthesis according to the invention are polylactic acid (PLA), glycolic acid/lactic acid copolymer (GLA), polydioxanone and blends thereof. Such an embodiment has the advantage of providing useful information to the surgeon at the moment of implantation of the prosthesis, without imposing on the patient the long-term presence of an excessive amount of foreign matter, the patch or patches being resorbed and disappearing at the end of a certain period of time after implantation.

The patch or patches of the prosthesis according to the invention may have any shape imaginable, for example a geometric shape such an oval, round or rectangle shape, or a graphical shape, such as an arrow, a symbol or even a letter or writing: in general, for the sake of minimizing the presence of foreign matter in the patient's body to the maximum, the patches are relatively small in size, the difference in colour relative to the base fabric to which they are grippingly fastened being sufficient to make them clearly apparent to the surgeon.

For example, a patch may take the form of an arrow so as to indicate to the surgeon the direction of insertion of the prosthesis.

The patch or patches of the prosthesis according to the invention are provided with at least one, and preferably several, barbs projecting from one of their surfaces. These barbs may project from said surface substantially perpendicular to the plane of said surface or alternatively along one or more planes inclined to the plane of said surface. These barbs are intended to function as fastening means, by penetrating into the openings and intermeshing in the yarns forming the openings of the apertured surface or surfaces of the base fabric of the prosthesis according to the invention due to the effect of the pressure exerted on a patch towards the base fabric. Advantageously, these barbs may also be withdrawn, by pulling on the patch, which can then be repositioned elsewhere on the apertured surface of the base fabric, if required, at the moment of manufacture of the prosthesis according to the invention.

Thus, a patch may be grippingly fastened, if necessary temporarily, to the base fabric of the prosthesis according to the invention. Thus, in one embodiment, the barb or barbs grippingly fasten the patch or patches to the apertured surface of the base fabric in a repositionable manner.

Alternatively, it is possible to fix the patch or patches to the apertured surface of the base fabric definitely by adding a spot of adhesive or a suture stitch between the patch and the base fabric.

The barbs are made of a biocompatible material, which may or may not be identical to the material forming the body of the patch. Thus, the barbs may be made of a material that may or may not have the same colour as the patch.

The patches of the prosthesis according to the invention may be produced by the injection moulding of a biocompatible thermoplastic.

In a preferred embodiment, the patches of the prosthesis according to the invention are made of a gripping fabric.

In the present application, the term "gripping fabric" is understood to mean a fabric having, on at least one of its surfaces, a plurality of hooks or barbs, arranged in a regular or random fashion, these projecting substantially perpendicular to said surface and being capable of penetrating the surface or the thickness of an apertured fabric on which it is applied. One example of a known gripping fabric is the gripping part of a "Velcro®" system. Thus, the barbs of the patches according to the invention may be formed from yarns, for example thermoplastic monofilament yarns, coming directly from the arrangement of yarns forming the patch. Such fabrics and barbs, and their manufacturing process, are for example described in the patent applications WO 01/81667, DE 198 32 634 or in the patents U.S. Pat. No. 6,596,002 and U.S. Pat. No. 5,254,133.

Alternatively, the barbs of the gripping fabric may be any hooks made of any biocompatible material, fastened to the arrangement of yarns forming said fabric, whether these hooks had been incorporated into said fabric during manufacture (braiding, knitting, weaving, etc.) of said arrangement of yarns or had been attached afterwards.

In a preferred embodiment, the barbs stem from the yarns used for knitting the gripping fabric. For example, the gripping fabric may comprise in general a lap of monofilaments initially forming small loops on the outside of said lap, each loop giving rise to two barbs projecting perpendicular to said lap after partial melting of the thermoplastic yarn initially forming the loop, as described in WO 01/81667.

Thus, the barbs of a patch of the prosthesis according to the invention, or alternatively the entire patch, may be made from intrinsically coloured yarns, i.e. yarns coloured by nature and without the deposition of an ink unfavourable to cell colonization. In particular, it is possible to use, for producing the barbs or the entire patch, coloured suture thread recognized as being biocompatible according to the regulations in force with regard to medical devices. Such thread suitable for producing the barbs or patches of the prosthesis according to the invention is for example the green polyester thread sold under the name "Surgi-Fil" by the company Roeko.

Preferably, the length of the barbs is defined so as to penetrate into and catch onto the apertured surface of the base fabric, preferably in a limited manner, that is to say if possible without passing from one side of the base fabric to the other.

The prosthesis according to the invention is thus very easy to produce.

For example, it suffices to produce a panel of gripping fabric with intrinsically coloured yarns, then to cut patches of the desired shape and size from this panel and then quite simply to make these patches grip the base fabric at the desired places by means of their barbs; moreover, it is also easy to remove these patches once they have been grippingly fastened and then to refasten them at more suitable places in the event of an error when first fastening them.

In a preferred embodiment, the gripping fabric used is itself apertured and/or porous, as defined above. Thus, once the patch has been grippingly fastened to the apertured surface of the base fabric, it in no way obstructs the openings in the apertured surface of the base fabric, thereby preserving its good cell recolonization capability. For example, the fabric structure of the patch comprises or defines, on its two surfaces, including that having the barbs, open pores having, for example, a diameter between 0.4 and 5 mm. In one embodiment, the patch may be provided with barbs on both its surfaces.

In a preferred embodiment of the invention, the patch is made of a gripping fabric as described in WO 01/81667 made of biodegradable yarns, the barbs being obtained from a thermoplastic monofilament. For example, each barb may have a length of between 1 and 2 mm and the barb density may range from 30 to 50 barbs per square centimeter: such a density makes it possible for the patch to be grippingly fastened to the base fabric and/or easily removed therefrom so as to be repositioned if so required.

When such a gripping fabric in the form of a patch is applied, barbs to the front, on the apertured surface of the base fabric, the barbs engage in the meshes or openings and between the yarns of the base fabric, and lock the patch onto the apertured surface of the base fabric. This locking effect, which is effective even in a liquid medium, is sufficient to fix the patch to the base fabric, while still allowing the patch to be unfastened so as to adjust its position relative to the base fabric, if so required.

Another aspect of the present invention is a kit comprising:

- at least one fabric called the base fabric and having at least one apertured surface, designed to be implanted in a specified position at an implantation site, as defined above; and
- at least one patch having a different colour from that of the base fabric, said patch being provided with at least one barb projecting from one of its surfaces, said barb or barbs being designed for grippingly fastening said patch to said apertured surface of said base fabric at a specific place on said surface. The patch of the kit according to the invention may be as described above. The kit according to the invention may comprise a plurality of patches as described above.

The advantages of the present invention will become more clearly apparent in the light of the following description and the appended drawings in which.

Figure 1:
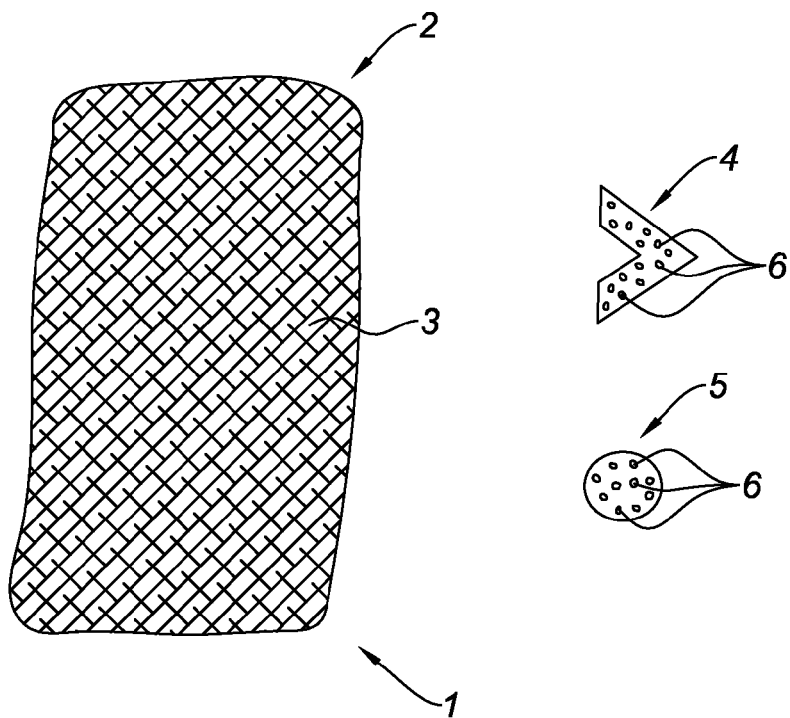
FIG. 1 is a top view of a kit according to the invention.

Referring usefully to FIG. 1, a kit according to the present invention is shown in general by the reference 1. The kit 1 comprises a base fabric in the form of a piece of fabric 2 of rectangular overall shape. This piece of fabric 2 may have an area ranging from 4 to 1600 cm$^2$ and may advantageously be used for repairing an abdominal wall hernia. The piece of fabric 2 has two surfaces, an apertured surface 3 of which is visible in the figure.

Such a fabric with at least one apertured surface may be obtained using the following method: a three-dimensional knit is produced on a 22-gauge Raschel knitting machine using six needle-guide bars threaded one full/one empty with white polyethylene terephtalate (PET) multifilament yarns (50 dtex; 22 filaments), using the following schemes, according to ISO 11676:

Bar 1: 1.2.1.1/1.0.1.1/1.2.1.1/1.0.1.1/1.2.2.2/3.2.2.2/1.2.2.2/3.2.2.2//

Bar 2: 1.2.2.2/3.2.2.2/1.2.2.2/3.2.2.2/1.2.1.1/1.0.1.1/1.2.1.1/1.0.1.1//

Bar 3: 0.1.0.1/0.0.0.0//

Bar 4: 0.1.0.1/0.0.0.0//

Bar 5: 1.1.0.1/1.1.2.1/1.1.0.1/1.1.2.1/2.2.2.3/2.2.2.1/2.2.2.3/2.2.2.1//

Bar 6: 2.2.2.3/2.2.2.1/2.2.2.3/2.2.2.1/1.1.0.1/1.1.2.1/1.1.01/1.1.2.1//

Bars 1 and 2 form one surface of the fabric, bars 5 and 6 form the opposite surface of the fabric and bars 3 and 4 form the spacer linking the two surfaces together.

Such a construction results in a white three-dimensional knit having openings measuring about 2.5×1.7 mm on both its surfaces.

Figure 2:
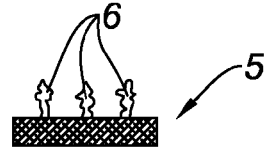
FIG. 2 is a cross-sectional view of a patch of a prosthesis according to the invention.

FIG. 1 also shows a first patch 4 and a second patch 5. The first patch 4 has the overall shape of an arrow and the second patch 5 takes the form of a disc. Each of these patches is provided with barbs 6 projecting perpendicular to one of their surfaces, as shown in FIG. 2, which is a cross-sectional view of the second patch 5. For example, the first and second patches (4, 5) may each have an area ranging from 0.5 to 6 cm$^2$.

In this example, the patches (4, 5) are made of a gripping fabric obtained in the following manner: a knit is produced on a 24-gauge weft knitting machine using 3 needle-guide bars. Bars 1 and 2, intended to form the body of the gripping fabric, are threaded one full/one empty with 0.09 mm diameter green polyethylene terephtalate (PET) monofilament yarns according to the following schemes, according to ISO 11676:

Bar 1: 1.0/0.1//

Bar 2: 4.5/1.0//.

Bar 3, intended to form the monofilament lap resulting in the barbs is threaded 1 full/3 empty with a 0.15 mm diameter green polylactic acid (PLA) monofilament yarn according to the following scheme, according to ISO 11676:

Bar 3: 3.4/0.0/2.1/5.511.

The barbs are then produced by melting the loops of the lap produced by bar 3 according to the method described in WO 01/81667.

The above construction also gives rise to a gripping fabric having apertured surfaces.

Figure 3:
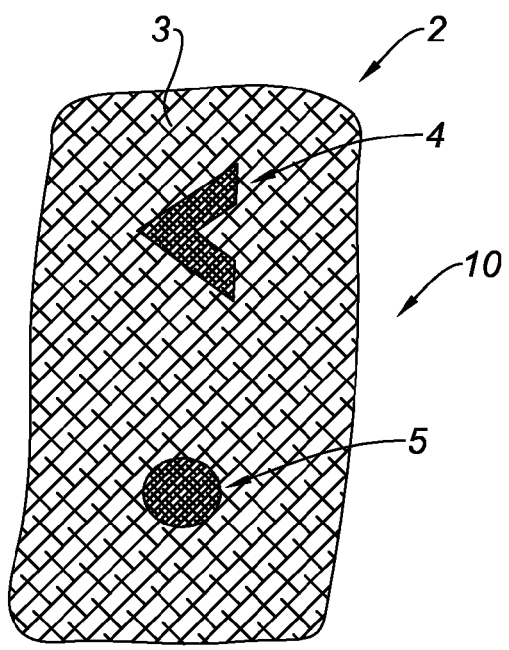
FIG. 3 is a top view of a prosthesis according to the invention.

FIG. 3 shows a prosthesis 10 according to the invention produced from the kit 1 of FIG. 1. To produce the prosthesis 10, first and second patches (4, 5), with the barbs 6 directed towards the apertured surface 3 of the piece of base fabric 2, have simply been applied and pressure exerted thereon. The first and second patches (4, 5) were applied at specific places on the apertured surface 3 of the base fabric so as to provide particular information to the surgeon carrying out the implantation.

The prosthesis 10 was thus produced in a simple and particularly rapid manner.

For example, the first patch 4 in the shape of an arrow can allow the surgeon to differentiate the left-hand part of the prosthesis from the right-hand part.

For example, the second patch 5, of round shape, may indicate to the surgeon the location of the median line of the prosthesis.

Because of their apertured structure, the first and second patches (4, 5) do not affect the good cell colonization capability of the base fabric. In addition, because of their colour, which differs from that of the base fabric, the patches are immediately visible and easily able to be interpreted by the surgeon.

The invention claimed is:

1. A prosthesis comprising:
   at least one base fabric having at least one apertured surface, and
   an information means comprising a plurality of gripping fabrics having a color different from that of the base fabric, each gripping fabric being provided with at least one barb projecting from a surface of the gripping fabric designed to fasten the gripping fabric to the apertured surface of the base fabric at a specific place on the apertured surface, the presence of the gripping fabric at the specific place bearing information designed to facilitate implantation of the prosthesis in said specific place, wherein the at least one barb is formed from a yarn coming from an arrangement of yarns which form the gripping fabric.

2. The prosthesis according to claim 1, wherein the base fabric has two apertured surfaces and one or more gripping fabrics are grippingly fastened to each of the two apertured surfaces.

3. The prosthesis according to claim 1, wherein the base fabric is a knit.

4. The prosthesis according to claim 1, wherein the base fabric is a two-dimensional knit.

5. The prosthesis according to claim 1, wherein the base fabric is a three-dimensional knit.

6. The prosthesis according to claim 1, wherein the base fabric is a combination of a two-dimensional knit and a three-dimensional knit.

7. The prosthesis according to claim 1, wherein at least one gripping fabric of the plurality of gripping fabrics is apertured.

8. The prosthesis according to claim 1, wherein at least one gripping fabric of the plurality of gripping fabrics is made of a biodegradable material.

9. The prosthesis according to claim 1, wherein at least a first gripping fabric of the plurality of gripping fabrics has an overall shape of an arrow.

10. The prosthesis according to claim 9, wherein at least a second gripping fabric of the plurality of gripping fabrics has a disc shape.

11. The prosthesis according to claim 10, wherein the first and second gripping fabrics each have an area ranging from 0.5 to 6 cm$^2$.

12. The prosthesis according to claim 1, wherein at least one gripping fabric of the plurality of gripping fabrics is removable and refastenable to the at least one base fabric.

13. The prosthesis according to claim 1, wherein the at least one barb has a length defined so as to penetrate into and catch onto the apertured surface of the base fabric without passing from one side of the base fabric to a second side of the base fabric.

14. A kit comprising:
at least one base fabric having at least one apertured surface, and,
a plurality of gripping fabrics having a different color from that of the base fabric, each gripping fabric being provided with at least one barb projecting from a surface of the gripping fabric, the at least one barb designed for grippingly fastening the gripping fabric to the at least one apertured surface of the base fabric, wherein the at least one barb is formed from a yarn coming from an arrangement of yarns which form the gripping fabric.

15. The kit of claim 14, wherein the yarn that forms the barb is a monofilament yarn.

16. The kit of claim 14, wherein at least one gripping fabric of the plurality of gripping fabrics is a knit.

17. The kit of claim 14, wherein at least one gripping fabric of the plurality of gripping fabrics is repositionable on the at least one base fabric upon removal from the at least one base fabric.

18. The kit of claim 14, wherein at least a first gripping fabric of the plurality of gripping fabrics has an overall shape of an arrow.

19. The kit of claim 18, wherein at least a second gripping fabric of the plurality of gripping fabrics has a disc shape.

20. A prosthesis comprising:
at least one base fabric having at least one apertured surface, and
at least one gripping fabric having a color different from that of the base fabric, the gripping fabric being provided with at least one barb projecting from a surface of the gripping fabric designed to fasten the gripping fabric to the at least one apertured surface of the base fabric at a specific place on the apertured surface, the presence of the gripping fabric at the specific place bearing information designed to facilitate implantation of the prosthesis in said specific place, wherein the at least one barb is formed from a yarn coming from an arrangement of yarns which form the gripping fabric, and the at least one gripping fabric includes at least a first gripping fabric having an overall shape of an arrow and a second gripping fabric including a disc shape.

21. A kit comprising:
at least one base fabric having at least one apertured surface, and,
at least one gripping fabric having a different color from that of the base fabric, the gripping fabric being provided with at least one barb projecting from a surface of the gripping fabric, the at least one barb designed for grippingly fastening the gripping fabric to the at least one apertured surface of the base fabric, wherein the at least one barb is formed from a yarn coming from an arrangement of yarns which form the gripping fabric, and the at least one gripping fabric includes at least a first gripping fabric having an overall shape of an arrow and a second gripping fabric including a disc shape.

* * * * *